United States Patent [19]
Engle et al.

[11] Patent Number: 5,567,328
[45] Date of Patent: Oct. 22, 1996

[54] MEDICAL CIRCUIT FORMING PROCESS

[75] Inventors: Paul F. Engle; Thomas J. Lynch, both of Mechanicsburg; Roger T. Banks, York, all of Pa.

[73] Assignee: The Whitaker Corporation, Wilmington, Del.

[21] Appl. No.: 482,244

[22] Filed: Jun. 8, 1995

[51] Int. Cl.[6] .................................. B44C 1/22; C23F 1/00
[52] U.S. Cl. ................................................ 216/13; 216/20
[58] Field of Search .................................. 216/13, 20, 33, 216/41, 36; 29/846; 427/96; 128/642

[56] References Cited

U.S. PATENT DOCUMENTS

| | | | |
|---|---|---|---|
| 5,041,187 | 8/1991 | Hink et al. | 216/20 X |
| 5,069,215 | 12/1991 | Jadvar et al. | 128/642 |
| 5,109,851 | 5/1992 | Jadvar et al. | 128/642 |

*Primary Examiner*—William Powell
*Attorney, Agent, or Firm*—Kevin D. McCarthy

[57] ABSTRACT

A process to manufacture disposable medical flat flexible printed circuits 10. The process entails depositing conductive metal in the range of 1000 to 2500 Angstroms thick onto a flexible film having a thickness in the range of 0.1 to 10 mils. The first portions of the conductive metal are covered with a resist material arranged in a pattern. Metal circuit material is deposited onto second portions of the conductive metal. Overplating the metal circuit material with a corrosion resistant metal. Lastly, removing the resist material and the first portions of the metal and laminating the circuit.

22 Claims, 3 Drawing Sheets

5,567,328

MEDICAL CIRCUIT FORMING PROCESS

FIELD OF THE INVENTION

The invention pertains to creating a disposable circuit for medical applications. More particularly, the circuit must permit a 75Ω per circuit resistance drop and be able to withstand medical applications.

BACKGROUND OF THE INVENTION

A configuration of flat conductive circuits on a substrate of flexible insulating material is well known. The circuits are fabricated on the surface of the substrate by a manufacturing process that is a subtractive process.

According to a typical subtractive process, an insulating substrate is laminated with copper foil covering the substrate making a three layer structure of substrate, adhesive and foil. The foil is covered by a photosensitive material that is resistant to a metal enchant. The photosensitive material is photoexposed by illumination, to sensitize the material for removal when washed. During photoexposure of the photosensitive material, an opaque mask casts a shadow over portions of the photosensitive material. The mask shadow is configured in a pattern of an electrical circuit. Thereafter, when the photosensitive material is washed, the unshadowed material is removed, leaving the shadowed material remaining in a pattern of a desired circuit on the substrate. The metal is then etched, hence, subtracted from the substrate, except where the shadowed material resists the enchant. Thereafter the shadowed material is cleaned from the metal that remains as the electrical circuit adhered to the substrate. The adhesive layer is a disadvantage because of mechanical and thermal instability of adhesives. In the example of a fine line circuit, the adhesive thickness is 0.001 inches and the circuit is 0.0007 inches thick by 0.005 inches wide, which cause both circuit positional tolerance and contact force problems. Customers want an adhesiveless solution.

It has been recognized that medical instruments such as esphogael electrodes require special printed circuit characteristics. One such electrode is disclosed for example in U.S. Pat. No. 5,069,215. Such a printed circuit characteristic is being able to withstand the daily medical applications.

The electrical circuit disclosed in the above referenced patent utilizes a silk screen method to create its circuitry. The silk screen method is a multiple step process. The process includes replacing a paper liner with a polyester carrier onto a base material. The substrate is then silkscreened with a silver ink (silver flakes or powder which is suspended in an organic media that is cured) circuit upon a polyester substrate after the substrate had an acrylic adhesive applied. The silver is partially cured so that the silver circuit can be inspected. The silver circuit is then insulated by a silk screening process. The insulation is cured and the circuits are then resistance tested. The paper liner then replaces the polyester carrier. This method produces circuits having 80,000–130,000 Å thick. This circuit thickness is too much for medical instrumentation because it is subject to cracking and silver is also deleterious in medical applications.

The circuit pattern required is a 12 lead circuit with ability to sustain a 5.0 MHz transducer mounted on the tip of medical instruments, like a gastroscope. Moreover, the circuit pattern has to carry an input impedance greater than 500 kohms at 10 Hz for a preamplifier along with a differential input gain of 220 Hz high-pass filters. The printed circuit must also deliver a constant current delivery continuously variable from 0–40 ma and a load impedance at a constant current at impedance up to 4000 ohms at 20 ma.

There is a need to create a circuit that is efficiently produced, have longer use due to the strains of medical applications and which permits a 75Ω per circuit resistance drop.

An additive process for disposable medical circuits would apply metal solely where needed on the substrate economically.

SUMMARY OF THE INVENTION

A disposable medical circuit created by depositing conductive material onto sputtered film. Depositing a mask in a pattern and plating a metal circuit material. Overplating the metal circuit material with a corrosion resistant metal. Removing the mask material. The circuit is finished by laminating a protective coverlayer.

Numerous other advantages and features of the present invention will become readily apparent from the following detailed description of the invention and the embodiments thereof, from the claims and from the accompanying drawings in which the details of the invention are fully and completely disclosed as a part of this specification.

DETAILED DESCRIPTION OF THE PREFERRED EMBODIMENTS

Figure 1:
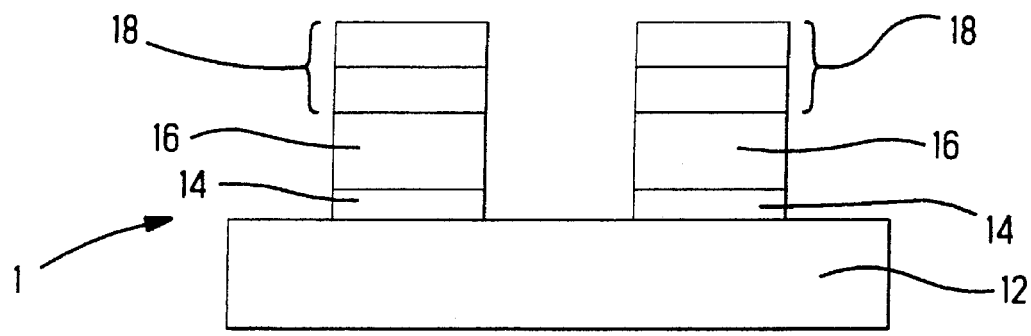
FIG. 1 is a partial, side view of the printed circuit.

While this invention is suspectable of embodiment in many different forms, there is shown in the drawing and will be described herein in detail a specific embodiment thereof with the understanding that the present invention disclosure is to be considered as an exemplification of the principles of the invention and is not intended to limit the invention to the specific embodiment illustrated.

The invention pertains to a cost effective process for small line spacing that is beneficial in medical technology. Normally, the cost of manufacturing circuits per conductor increases as the centerline spacing decreases because the cost of the small flat copper wires increases faster than the consumption of plastic decreases. In this case, the cost declines because cost is proportional to circuit area. The process has a short cycle time. A particular advantage is the ability to achieve fine resolution and close dimensional tolerances in masking and in circuits produced by masking. Another particular advantage is the ability to produce economically thick or thin, low density circuits on a surface. The mass and volume of discarded waste products is kept to a minimum, enabling economical production. Another advantage is the adhesiveless nature of and process, with the metal directly bound to the substrate.

With reference to FIG. 1 and FIG. 3, step one of the process comprises sputtering a thin film of metal 14 onto an organic surface, for example, a surface of a plastic film 12. The metal 14 can also be a thin film that is laminated to the plastic film 12. The metallized plastic film has such a thin metal layer 14 that the film 12 retains its original flexibility prior to being metallized. Bending and flexing of the film 12 can occur without cracking the metallized layer 14.

The organic surface is a plastic film 12 like the following: (I) Poly (ethyleneglycol, terephthalate), (II) Poly (propylene) (III) Polyethylene, (IV) Poly (vinylidene difluoride), (V) Polyimide, (VI) Poly (1-butene), (VII) Poly (4-methyl-1-pentene), (VIII) Poly (vinyl chloride), (IX) a liquid crystal polymer, Polyurethane, or Poly (ethylene naphthalate) (X).

The film 14 of metal is any conventional conductive material able to provide a 75Ω per circuit resistance drop and can be composed of any suitable metal or metals, such that the resultant coating is conductive, is capable of being sputtered, and is removable in a process such as etching. If more than one metal is employed, the metals can comprise, alloys, materials in a layered structure or laminated structure, or a seed layer of one metal, e.g. Cr, Ti, Sn, or Ni; under the principle layer, e.g., Cu. Suitable metals comprise Copper, Aluminum, Tin, Titanium, Nickel, Iron, Silver, Gold, Palladium and oxides thereof. Tin, Iron, Copper, Silver, Aluminum, Titanium can be utilized as a base material as long as there is an overcoat layer of a metal that has no negative effects on the human body, such as Nickel, Gold, Palladium and mixtures thereof. A special case is the deposition of conductive compounds like Titanium Nitride by sputtering Titanium in a nitrogen atmosphere. These compounds have excellent conductivity and corrosion resistance.

The thin film of metal 14 is sufficiently thin to allow flexing of the metallized film 12, flexibility is not an issue, i.e. 10,000 Å does not greatly effect flexibility, and to be removed to produce a minimum of waste products. The thin film of metal 14 is sufficiently thick to conduct electricity in an electroplating bath, approximately 800–1200 Angstroms, and preferably 2500 Å. The thin film of metal 14 can be applied by one or more techniques comprising; sputtering, electroless plating on a catalyzed surface of the film, vacuum deposition, lamination, or chemical vapor deposition, CVD. Particularly, the first hundred angstroms of the copper or nickel is sputtered to gain the superior adhesion of metal to flexible film that results from sputtering and the remaining desired thickness would be evaporated to gain the superior economics of evaporation. In the case of low pressure techniques, i.e., sputtering, vacuum deposition or CVD, the degree of adhesion of the thin metal film can be controlled by one or more pretreatments such as, plasm etches, oxygen plasma, and by addition of select atmospheres like argon. For example, layers like Ni, Cr, Ti, Fe or their alloys with copper or each other may be employed to promote adhesion. Controlling adhesion permits production of a product that has characteristics such as rigorous adhesion to the plastic film 12 or lacking adhesion to permit easy removal, depending upon the desired film characteristics.

By way of example, metal such as copper having a thickness, for example, 1000 to 2500 Angstroms thick, is applied onto an organic surface, such as a surface of a plastic film 12. The copper is sputtered on 2 to 7 mils thick, flexible polyester film. For example, the film 2 can be polyimide or polypropylene. Nickel, Palladium, Silver, and Aluminum can be used instead of Copper.

Figure 2:
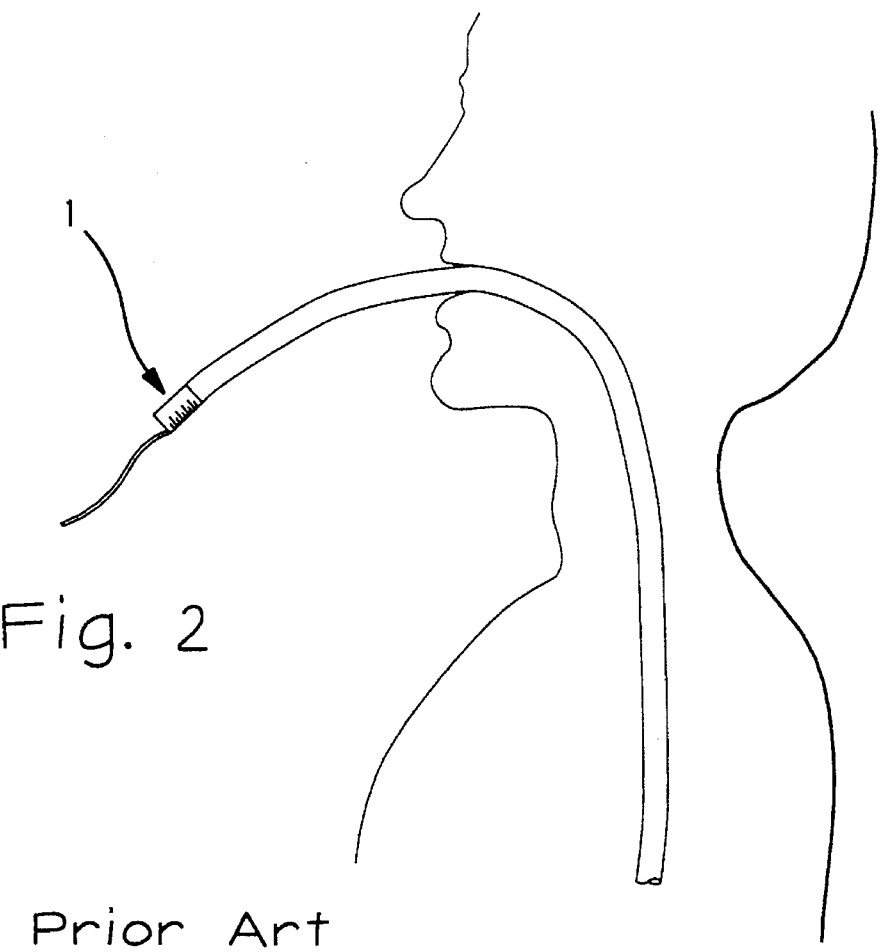
FIG. 2 is a schematic of the printed circuit applied to a medical instrument.
Figure 3A:
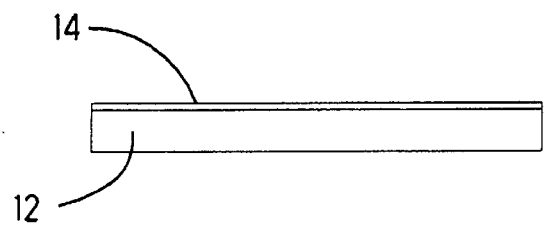
FIG. 3 is a schematic of the process of manufacturing the present printed circuit.
Figure 3B:
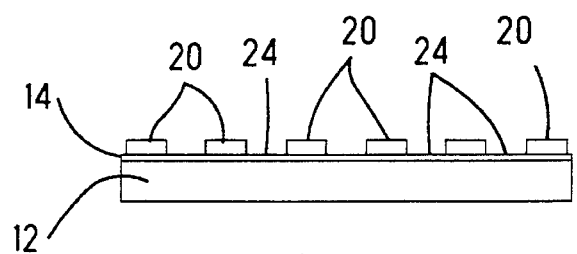
Figure 3C:
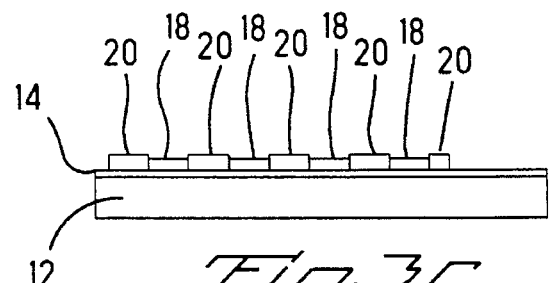
Figure 3D:
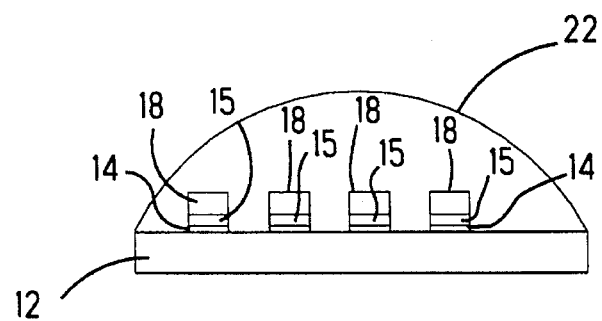
Figure 4:
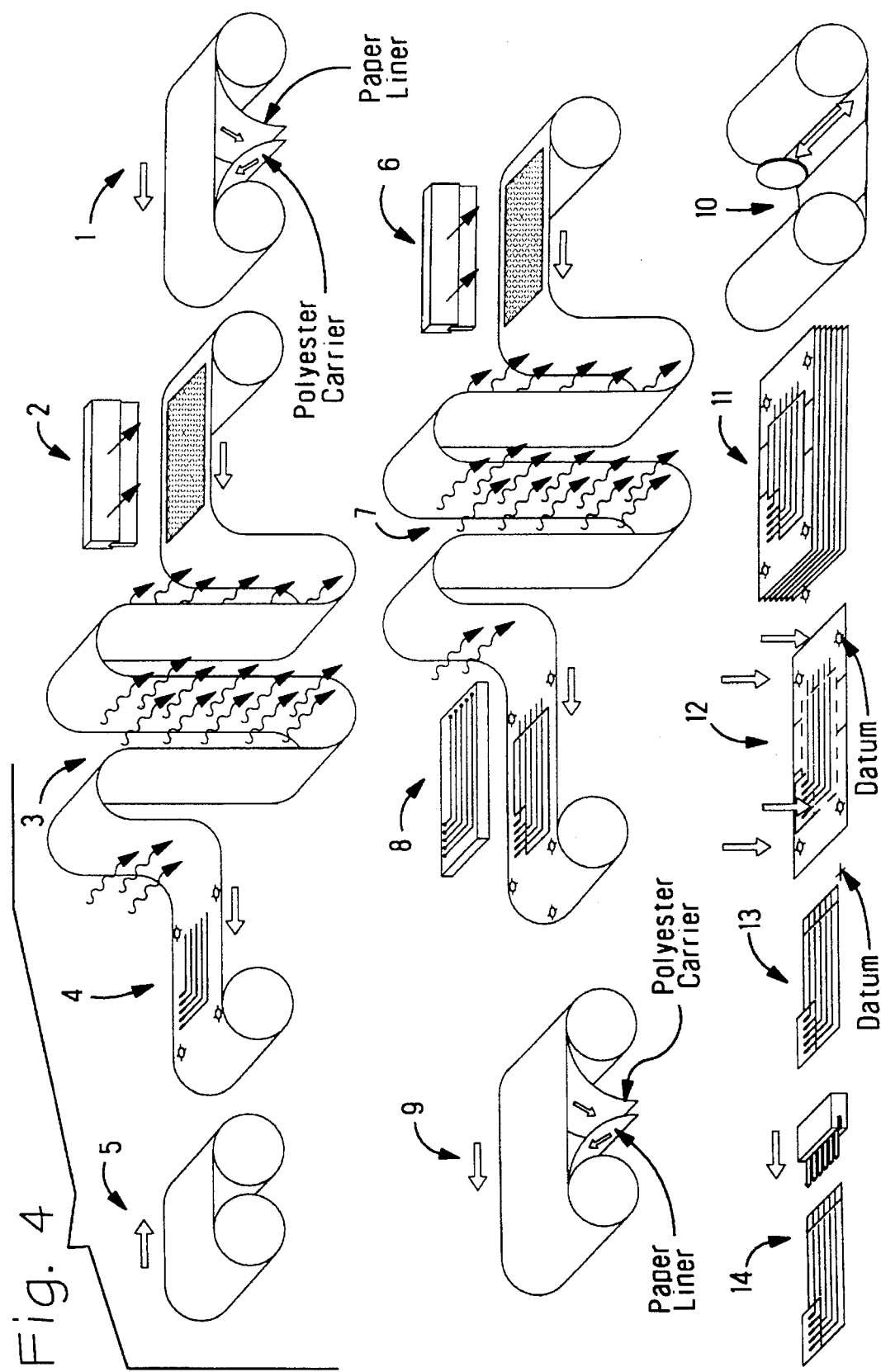
FIG. 4 is a schematic of the prior art process to make medical instrument printed circuits.

With reference to FIG. 2, the metallized surface 14 of the plastic film 12 is coated with an adhering nonconductive material, referred to as a mask 20, that is resistant to an electrochemical plating bath. The normal photosensitive mask 20 materials are expensive, $20–200 per pound, and contain reactive chemicals like quinone and hydroquinone which can affect plating, even residually. The styrene/maleic anhydride and styrene/acrylate copolymers of this invention are cheap, $2/lb and relatively benign to plating. The constituents of such a bath are commercially available with either acidic or basic pH.

The mask material 20, moreover, should be in a foamed state rather than a bubble-free form. In most instances, a mask 20 is bubble-free by adding any conventional anti-foam material such as silicones, fluoropolymers or the like. Anti-foam materials are usually applied to mask compositions because the viscous polymer solution traps air which does not leave the mask upon drying. A foamed mask produces a thicker mask than a bubble-free mask, thereby it is also more economical since less mask material is required. The foamed mask furthermore produces a tougher film because the stress and strain absorbing abilities of the foam bubbles prevent micro-cracks from forming on the film as the mask 20 dries. Lastly, removal of the foamed mask material during the demasking stage is easier because there is less material to remove and the mask surface area is significantly greater once the demasking solution starts to open the bubbles.

The nonconductive material is arranged in a mask pattern 20 that covers selected areas of the metallized surface 14 of the plastic film 12. Areas of the metallized surface 14 that remaining uncovered by the mask pattern 20 define an electrical circuit pattern 24. The mask pattern 20 defines covered areas of the metallized surface 12 that will not contain an electrical circuit. The mask pattern 20 circumscribes the circuit pattern 24. The electrical circuit pattern 24 is a mirror image of a planar electrical circuit that comprises, a flexible flat cable or other types of electrical circuit having different circuit patterns.

The material comprising the mask has the following characteristics; (1) be a semipermanent mask that is mechanically stable and chemically resistant to subsequent process steps that will be described hereinafter, (2) be chemically and mechanically stable in plating baths and associated plating processes, (3) be easily removable with selection of the proper processing line conditions, e.g., bath pH, complexing agents, temperatures, and other line conditions.

Suitable mask material comprises; UV light and visible light curable photomasks (A), waxes like petroleum wax (B), and specialty polymers (C) like copolymers of Styrene and Maleic Anhydride and Acrylates, or Acrylic copolymers. Typically, metal plating baths have a low pH. A mask material stable when exposed to such baths would be stable in the range equal to or less than pH 5, and would be dissolvable to facilitate its removal in a pH range of 8 to 11. The above ranges are characteristic of the properties of the above-described copolymer systems.

The mask material should be capable of edge resolution such that pattern features can be produced with a dimensional tolerance of equal to or less than plus or minus 10% of the subject line width. For example, a line of 0.050 inch (0.125 cm) would have a tolerance which was no greater than that of plus or minus 0.0025 inches (0.005 cm). Particularly desirable is a mask material that is capable of being applied by a continuous process. For example, a continuous mask applying operation applies one or more mask patterns onto a metallized plastic film at a speed that is synchronous with that of the film as the film is continuously reeled out, moved through a plating bath at a speed that will allow plating of a metal layer of a desired thickness onto the metallized plastic film. The mask is applied to the moving, metallized plastic film to apply a circuit pattern on the film prior to the film moving through a plating bath that plates metal onto the circuit pattern.

A desirable application technique involves a computer software driven control that generates a correction to the mask application stage in response to feedback signals generated from continuous measurement of variations in the production of the mask and/or variations in the production of the plating produced by the plating bath. This desirable application technique can be particularly suited by an ink jet printer.

Another desirable application technique involves a rotating screen printer. The rotating screen printer uses a seamless rotary screen that has holes perpendicular to the axis of the drum, or has the holes the conventional nine degrees off perpendicular. A squeegee presses the ink in the screen through the perforated screen wall on to the metallized plastic film. A pump and a level control guarantee a constant ink supply. Higher squeegee pressure results in more ink delivery on the metallized film. Thus, squeegee pressure determines the quantity of ink delivered. By utilizing a rotating screen printer the metallized plastic film can have a width ranging from millimeters to over three meters which makes this application technique so valuable.

In particular, the film 12 needs to be pre-conditioned in a web pre-conditioner. The web pre-conditioner pre-shrinks the film at a temperature equal to or greater than the maximum temperature that the film or circuit will experience in later processing or in final service life.

Rotating screen printing and a laser jet printing are distinct in numerous ways. Such obvious distinctions include 300 dots per inch to 600 dots per inch difference and also comparing the masks to a stored computer file versus instantaneous feedback system that allows for immediate correction. These two printing methods do provide excellent masks, in particular the laser jet printing method.

In one embodiment, the original metallic film 1 can be sufficient for the electrical circuit requirements, which allows the mask to be applied at a speed that allows synchronization with a moving metallized plastic film without regard as to whether variations in plating are being affected. A software driven ink jet printer is a convenient implementation as well as a rotating screen printing method.

By way of example, the mask pattern 20 is made using a resist material, also known as a resist, via an ink jet printer, not shown, a rotating screen printer like produced by Stork® or Nordson® not shown, a roller wheel printer not shown, or a rotogravure process, not shown. One resist is a Styrene Acrylate polymer, available from AMP Incorporated, Harrisburg Pa. 17105. The resist material is resistant to acidic chemical baths. Alternatively, an ink that has resist properties, and that is resistant to basic, rather than acidic chemical baths is applied. The ink is commercially available from Dataproducts Corporation, 6250 Canoga Avenue, Woodland Hills, Calif., Telephone Number (818) 887-3803.

An ink jet printer is commercially available, for example, from Dataproducts Corporation. Other commercially available, ink jet printers can be used. The printer applies a resist material to a flexible composite sheet of polyester and copper. The printer applies resist having a viscosity that flows through a printing jet nozzle of the printer. The printer has the capability of applying resist in a layer of about 0.001 inches thick or thicker. A preferred dot pattern of 300 dots per inch, with an average of 4.7 mil. dot diameter when applied on a square grid of 3.33 mil. grid size. Four colors of resist can be used. The colors are combinations of 10% to 100% of magenta, cyan, yellow and black.

The printer head on which one or more nozzles are mounted can be displaced with respect to the composite sheet, at a speed of six inches (15.24 cm.) per minute.

One construction of a printer provides two heads, each at an angle of 7 degrees from the horizontal. Each head has 48 nozzles distributed along 60 inches (152.4 cm.) along the angle. Accordingly, two rows of nozzles, a total of 96 nozzles is provided. Another construction of a printer provides four head, each mounted on a shuttle one at a time. The speed of printing dots is one foot per second for one layer of dots having a layer thickness of 0.001 inch and a pattern of dots at 0.5 inch (2.54 cm.) wide, at 5,000 dots per second, with dots having a diameter of 4.7 mil.

The following speeds are achieved. Using the construction of two heads, passing the heads over a horizontal composite sheet of 5 feet width, each pass achieves 120 seconds per foot, or a speed of 6 inches per minute is achieved. For maximum speed, two fixed heads with a total 90 nozzles are used, and the pattern applied by the nozzles working intermittently is driven by a computer which turns on and off the nozzles. The speed achieved is 60 feet per minute. Speeds up to 100 feet per minute are attainable.

The thickness of a resist material, comprising the mask pattern 20, is achieved by varying the weight from 50–150 Nanograms, with 150 Nanograms preferred. The thickness is further varied by repeating the pattern of dots on top of one another. The gram usage of resist material is 150 nanograms per drop, times 90,000 drops per square inch, or 0.0135 grams per square inch, or 1.944 grams per square foot for a 0.001 inch layer thickness.

The following print samples were produced using a Material ID, see column title below, supplied by AMP Incorporated to Dataproducts Corporation who used their commercially available printer to apply a pattern of resist material having an Ink ID, see column title below.

| Sample ID | Material ID | Ink ID | Comments |
| --- | --- | --- | --- |
| 5/26/94-1A | Cu/bkg | SI2-K1 | |
| 5/26/94-2A | Cu/bkg | SI2-M2 | |
| 5/26/94-3a | Cu | SI2-K2 | minimum wetting material, remelt puddles |
| 5/26/94-4A | film | SI2-M1 | poor ink adhesion |
| 5/26/94-5A | film | SI2-K3 | poor ink adhesion |
| 6/1/94-1A | film | XM7-M3 | very low PZT drive, light ink |
| 6/1/94 | Cu/bkg | XM7-M4 | remelt good flow |

The following observations of the samples were made. Light print and extraneous small dots on sample Jun. 1, 1994-1A were created by the way that particular print head (different from the May 26, 1994 tests) was initially set up for tests using this ink. The sample Jun. 1, 1994-1A was made with the proper drive levels, The key element shown on the two samples date Jun. 1, 1994 is increased adhesion of ink to the media material. The media material general wetting characteristics impeded ink flow as printed. The same Jun. 1, 1994-2A shows excellent coverage with image remelt. Some inks are not very compatible with some materials, while the XM7 ink was significantly more effective. Other useful processes, beside ink jet printing, include rotary screen phase transfer printing, flat screen printing, rotary screen printing and rotogravure printing.

With reference to FIG. 3, (A–D) one or more layers of resistant layer metal 16 are applied onto the exposed metallized plastic surface. The metal 16 can be any suitable layer or layers of elemental metal, alloy or combination thereof the metals 16 comprise; Gold, Palladium and Nickel. Alloy comprise: Palladium-Nickel.

The corrosive resistant metals 18 that overlay circuit metals 16 comprise an inert metal that has no negative effects on the human body. Such metals include Nickel, Gold and Palladium. More preferably, corrosive resistant layer is 30 microns thick, particularly using Gold.

For example, the circuit and corrosive resistant metals 16 and 18 are applied by electroplating according to known processes. The exposed metallized plastic surface comprises the circuit pattern 24. The metal applied to the exposed areas will form conductive areas of an electrical circuit. By way of example, Copper is additively grown electroless or electrochem in areas on the film exposed (0.5 to 5.0 mils. thick).

EXAMPLE 1.

A laminated film of polyester and copper was supplied by AMP Incorporated, and was printed by Dataproducts Corporation with a pattern of resist material supplied by Dataproducts Corporation. Copper was sputtered on the substrate. The pattern of resist had an image resolution of 6 mil. wide lines and 6 mil wide exposed areas. A commercially available Copper Sulfate bath was used at room temperature, having a 1.9 pH. The resist was removed by a mild Sodium Hydroxide stripper, commercially available. The circuit was then finished with a corrosion resistant gold layer and laminated by a dielectric coating of polyurethane.

EXAMPLE 2.

A laminated film of polyester and copper was supplied by AMP Incorporated, and was coated with a resist material, part number 985699-1, or part number 985720-1, available from AMP Incorporated. After 100° C. temperature drying of the resist material, two samples were immersed in a commercially available copper plating bath having a 1.9 pH at 65 Degrees Centigrade. No damage to the resist material by the bath was observed. The resist material was then stripped in an alkaline bath.

With reference to FIG. 3, the mask pattern 20 is removed to expose the very thin, metallized plastic surface 14 that was covered by the mask pattern 20. Thereafter, the very thin metallized plastic surface 14 is etched to remove the very thin metal 14 thereon, leaving only the plastic surface 12. The plastic surface 12 electrically isolates the electrical circuits. A desirable economic and environmental process feature will now be discussed. When the metal 14 is removed with an acidic medium, the spent medium is suitable for use as plating bath feed for metallizing the organic surface 12, if the metal plating is the same as that to be plated onto the organic surface 12.

By way of example, the uncovered sputtered copper 14 is etched, and the resist 20 is stripped in base or solvent to remove, leaving the covered copper 14 of substantial thickness and providing electrically conductive circuits. The conventional circuit etching process utilizes a cupperic chloride solution (a concentrated aqueous $CuCl_2$ and HCl). The conventional etching process normally entails a 1–3 minute etch and exposure time has to be controlled at 400 milliseconds. This conventional process is adaptable to the present invention, however, this conventional process requires uniform wetting by the etchant bath and reusing by the wash/neutralization solution is extremely difficult to complete with uniform quality in this short time period. An etchant can be diluted and its pH increased to slow the dissolution rate by the desired factor of 100–300::1. These measures to the etchant, however, are not as effective as a controlled current electrochemical etch. For example, a sputtered metal thickness of 5000 Å and atomic volume of copper at 11.869 (Å)$^3$ per atom, the removal rate per square inch of sputtered surface is 2.91 minutes with 50 milliampes current (using Faraday's law of equivalents (I*t)/F). In particular, ammonium phosphate is also suitable for removing the mask and sputtered conductive metal in a single step.

The circuit containing film 12 is carefully dried to remove surface water and absorbed water. A flexible flat cable is produced by this process when the circuits comprise conductors that are closely spaced together. The circuits can be in any planar pattern.

According to a further process step, a plastic film is laminated over the circuit as an insulator. The plastic film chosen as an insulator to cover the completed circuit can be any of the above plastic films referred to as being suitable for the metallized plastic film. Commonly a solventless ultraviolet light curable conformal coating or a polyvinyl chloride suspension is a plasticizer (like butyl phthalate), are used as cover layers that are low cost and effective. This plastic film does not require the chemical stability as the metallized plastic film that must survive-chemical plating and chemical etching baths.

According to a further process step, terminators, such as electrical contacts, are applied to the circuits, for example, by soldering.

EXAMPLE 3

A circuit is produced according to the following process; (1) sputter 2500 Å thick Copper onto 0.001 inch (0.0025 cm.) thick polyester film, (2) apply the circuit masks by ink jet printer, (3) plate Nickel and Gold onto circuit patterns circumscribed by the masks to the desired thickness, e.g. Nickel plated to 100 microns and then overplated with Gold up to 30 microns, (3a) select plate with Tin in crimp areas (at most a quarter inch at end of external circuit), (4) remove the masks, (5) use sulfuric acid or cuprous chloride to remove the residual Copper film with the circuit being protected by the Gold, (6) clean and dry the circuit on polyester, and (7) laminate a second layer of polyester (22) to protect the circuit.

Because additional metal is plated over the copper, e.g., Gold, selective etching can be done to remove metal only where it is not desired.

In the other embodiment, a method of making flexible flat cable having a two-tiered resist layer is disclosed. This method is designed for preparing flat flexible cable.

The process is the same as the one-tiered resist layer method set forth above of FIGS. 1–4; except the resist layer is deposited onto the metallized flat flexible film differently. The major difference is that the resist pattern depth at the edges of the conductive material be equal or greater than the depth of the desired conductive material; while the remaining resist layer not at the edges of the conductive material is of sufficient depth to prevent electrochemical growth of the conductive material. These different layers of resist, at the edges of the conductive material and the remaining areas to be masked, can be applied by the same instruments as set forth above. These instruments are merely altered to provide differing layers.

In particular, ink jet printing is conducted with high spacial resolution and multiple passes. The first pass masks the entire area which will not become a circuit to a depth of about 0.0001 inch and subsequent passes build the edge to the desired depth of the circuits. In Example 1 the mask at the desired circuit depth and position was 0.003 inch thick but only 0.005 inches wide. In this example only four percent of the material is required to serve as mask. This low percentage can be illustrated by the following chart:

| | |
|---|---|
| Total Metalized area: | 144 in² |
| Total Masked area: | 115.2 in² |
| Mask at 0.003 inch thick: | 0.35 in³ |
| Length of circuits @ 0.25 inch wide: | 115.2 in |
| Border mask at 0.003 * 0.005 inches: | 0.0035 in³ |
| Total mask by claim: | 0.015 in³ |
| Savings 1-(0.015/0.035) * 100 = | 95.7% |

The other printing methods can also provide a second tier resist layer. As a matter of course, the other printing methods apply subsequent layers through other screens, rotogravures or roller wheels to the desired resist level in the desired locations, as set forth above.

The difference between foamed and bubble-free mask can be best illustrated in the following example: a mask material comprising 74% Joncyryl 74, 14.5% Joncryl 85, 9.5% Joncryl 585 and 2% NH₄OH solution was applied to a film of 3000 Å of copper sputtered onto 0.003 inch thick polyester film, with and without an anti-foam agent.

With an anti-foam agent, the mask was 0.0006 inches thick. Upon plating, the product produced traces which were 0.0013 inch thick. The plated material was covered with a fine dust of copper particles as it exited the plating bath with a bubble-free mask. These fine particles were easily brushed off the surface and are the result of microcracks in the mask.

The experiment was repeated without an anti-foam and the mask was 0.0015 inch thick. Upon plating, the product traces were 0.0017 inch thick. The fine copper dust was essentially absent showing the great reduction in microcracks.

Many changes, modifications, variations, and other uses and applications of the subject invention will, however, become apparent to those skilled in the art after considering the specification and the accompanying drawings which disclose preferred embodiments thereof. All such changes, modifications, variations and other uses which do not depart from the spirit of the invention are deemed to be covered by the invention which is limited only by the claims that follow.

The applicants claim:

1. A process to manufacture disposable medical flat flexible printed circuits 10 comprising
    depositing conductive metal in the range of 1000 to 2500 Angstroms thick onto a flexible film having a thickness in the range of 0.1 to 10 mils.,
    covering first portions of the metal with a resist material arranged in a pattern,
    depositing metal circuit material onto second portions of the metal,
    overplating the metal circuit material with a corrosion resistant metal,
    removing the resist material and the first portions of the metal and
    laminating the circuit with a polymeric material.

2. A method as recited in claim 1, wherein the resist material pattern has at least two depths, at the edges of the second portions of the metal the resist material is equal or greater than the desired depth of the metal circuit material and the remaining first portions of the metal is coated sufficiently with the resist material to prevent electrochemical growth of the metal circuit material.

3. A method as recited in claim 1, and further comprising: removing the resist material with a solvent.

4. A method as recited in claim 1, and further comprising: removing the first portions of the metal with a metal enchant.

5. A method as recited in claim 1, wherein the resist material is a foamed material.

6. A method as recited in claim 1, wherein the first few 100 Å of conductive metal is sputtered and the remaining conductive metal is evaporated onto the flexible film.

7. A method as recited in claim 1, wherein the conductive material is selected from a group consisting essentially of Nickel and oxides thereof, the circuit material is selected from a group consisting essentially of Nickel and oxides thereof, and the corrosion resistant metal is a Gold layer.

8. A method as recited in claim 7, wherein the Nickel layer is about 100 microns and the Gold layer is 30 microns.

9. In a method to manufacture disposable medical flat flexible printed circuits 10 by ink jet printing, wherein a pattern of ink is applied by an ink jet, the improvement comprising:
    applying a pattern of an ink resistant to basic chemical baths by ink jet onto a composite sheet constructed of a first metal covering a polyester,
    depositing metal circuit material onto the metal without depositing the metal onto the ink,
    overplating the metal circuit material with a corrosion resistant metal,
    removing the ink and the first metal to provide a circuit on the sheet, and
    laminating a second layer of polyester to protect the circuit;
    wherein the ink resistant has at least two depths, at the edges of the pattern the ink resistant is equal or greater than the desired depth of the metal circuit material and the remaining pattern is coated sufficiently with ink resistant to prevent electrochemical growth of the metal circuit material.

10. A method as recited in claim 9, wherein the conductive material is selected from a group consisting essentially of Nickel and oxides thereof, the circuit material is selected from a group consisting essentially of Nickel and oxides thereof, and the corrosion resistant metal is a Gold layer.

11. A method as recited in claim 10, wherein the Nickel layer is about 100 microns and the Gold layer is 30 microns.

12. A method as recited in claim 9, wherein the resist material is a foamed material.

13. A method to manufacture disposable medical flat flexible printed circuits 10 comprising the steps of:
    Sputtering 100 to 300 Angstroms and evaporating 2700 Angstroms thick conductive layer onto polyester film having a range of thickness from 0.001 inch (0.0025 cm.) to 0.10 inch;
    Applying circuit masks,
    Plating a Nickel onto circuit patterns circumscribed by the masks to produce a circuit having a desired thickness;
    Plating a Gold layer to the desired thickness onto the Nickel;
    Removing the masks to expose the Copper film; and
    Removing the Copper film exposed by removal of the masks with the Nickel circuit being protected by the Gold;

Cleaning and drying the circuit and the polyester film, and laminating a second layer of polyester on the circuit to protect the circuit.

14. A method as recited in claim 13, wherein the circuit mask has at least two depths, at the edges of the circuit pattern the mask is equal or greater than the desired depth of the metal circuit material and the remaining masked area is coated sufficiently to prevent electrochemical growth of the metal circuit material.

15. A method as recited in claim 13, wherein the circuit masks is a foamed material.

16. A method as recited in claim 13, wherein the conductive material is selected from a group consisting essentially of Nickel and oxides thereof, the circuit material is selected from a group consisting essentially of Nickel and oxides thereof, and the corrosion resistant metal is a Gold layer.

17. A method as recited in claim 13, wherein the conductive material is selected from a group consisting essentially of Copper and oxides thereof, the circuit material is selected from a group consisting essentially of Nickel and oxides thereof, and the corrosion resistant metal is a Gold layer.

18. In a method to manufacture disposable medical flat flexible printed circuits 10, wherein a pattern of ink is applied by a seamless rotary screen, the improvement comprising:

pre-conditioning the polyester by exposing it to a temperature that is equal to or greater the maximum temperature the film or circuit will experience in later processing or in final service life;

applying a pattern of an ink resistant to basic chemical baths by a seamless rotary screen onto a composite sheet constructed of a first metal covering a flexible film, depositing metal circuit material onto the metal without depositing the metal onto the ink, and removing the ink and the first metal to provide a circuit on the sheet.

19. In a method as recited in claim 18, wherein the ink resistant has at least two depths, at the edges of the pattern the ink resistant is equal or greater than the desired depth of the metal circuit material and the remaining pattern is coated sufficiently with ink resistant to prevent electrochemical growth of the metal circuit material.

20. In a method as recited in claim 18, the improvement comprising the step of: laminating a second layer of polyester to protect the circuit.

21. In a method as recited in claim 18, the improvement comprising the step of: laminating a second layer of polyester to protect the circuit, and providing holes in the second film to permit access to the circuit.

22. A method as recited in claim 18, wherein the resist material is a foamed material.

* * * * *